United States Patent [19]
Glover et al.

[11] Patent Number: 5,457,273
[45] Date of Patent: Oct. 10, 1995

[54] PROCESSING WASTE SOLIDIFICATION

[75] Inventors: Edward C. T. S. Glover, London; Martyn S. Glover, Herts; John R. Fyson, London, all of England

[73] Assignee: Eastman Kodak Company, Rochester, N.Y.

[21] Appl. No.: 78,202

[22] PCT Filed: Dec. 16, 1991

[86] PCT No.: PCT/EP91/02415

§ 371 Date: Jun. 17, 1993

§ 102(e) Date: Jun. 17, 1993

[87] PCT Pub. No.: WO92/11213

PCT Pub. Date: Sep. 7, 1991

[30] Foreign Application Priority Data

Dec. 18, 1990 [GB] United Kingdom ............ 9027425

[51] Int. Cl.$^6$ ................. A62D 3/00; B09B 3/00
[52] U.S. Cl. ............. 588/252; 405/128; 488/249; 210/751
[58] Field of Search ............ 405/128, 129; 588/249, 256; 210/751, 762

[56] References Cited

U.S. PATENT DOCUMENTS

| | | | |
|---|---|---|---|
| 4,353,749 | 10/1982 | Ray et al. | 588/256 |
| 4,354,942 | 10/1982 | Kaczur et al. | 588/256 |
| 4,518,508 | 5/1985 | Conner | 588/256 X |
| 4,600,514 | 7/1986 | Conner | 210/751 |
| 4,601,832 | 7/1986 | Hoogkaas | 588/256 X |
| 4,666,490 | 5/1987 | Drake | 588/256 |
| 4,668,124 | 5/1987 | Pitts et al. | 588/246 |
| 5,205,906 | 4/1993 | Grutsch et al. | 210/762 X |
| 5,234,498 | 8/1993 | Graves | 588/256 X |
| 5,264,135 | 11/1993 | Mohn | 588/256 X |
| 5,275,509 | 1/1994 | Honeycutt | 588/2.55 |
| 5,285,000 | 2/1994 | Schwitzgebel | 588/256 |

FOREIGN PATENT DOCUMENTS

| | | |
|---|---|---|
| 0181010 | 5/1986 | European Pat. Off. . |
| 2098777 | 3/1972 | France . |
| 1432091 | 4/1976 | United Kingdom . |

OTHER PUBLICATIONS

World Patents Index Latest, JP, A, 60 237 398, Nov. 1985.
World Patents Index Latest and Patent Abstracts of Japan, JP, A, 63 291 680, 29 Nov. 1988.
World Patents Index Latest, JP, A, 63 291 679, 29 Nov. 1988.

*Primary Examiner*—Dennis L. Taylor
*Attorney, Agent, or Firm*—John R. Everett

[57] ABSTRACT

A method of treating photographic effluent containing one or more metal ions with an oxidation number greater than one, comprising the addition of a water-soluble silicate to the effluent in an amount to render it glass-like and less permeable to water. Conveniently the effluent has been treated by the addition of calcium hydroxide and the silicate, preferably water-glass may then be added either to the treated effluent suspension and the mixture separated or to the pre-separated solid.

10 Claims, No Drawings

PROCESSING WASTE SOLIDIFICATION

This invention relates to solidification of solid processing waste and in particular to solidification of photographic waste to render it more environmentally acceptable.

The overflow from a photographic processor will typically consist of environmentally undesirable substances such as heavy metal ions, sequestering agents, substances that have a high oxygen demand and colour developing agents and their derivatives, straight disposal of which contravenes sewer regulations in many parts of the world. It is therefor essential that the overflow is converted by chemical or physical means to a liquid which can be poured into the sewer and/or a residual solid which can be removed to a place of safe and legal disposal.

The use of an alkali metal silicate as one additive in treating certain industrial processing waste, such as radioactive and metal plating wastes, has been disclosed, for example, in Japanese Patent Publication No. 60237398 and U.K. Patent No. 1432091 respectively.

Co-pending PCT application No. PCT/EP 91/01680 and PCT/EP 91/01681 describe the addition of chemical reagents to precipitate, adsorb or otherwise remove harmful pollutants in particular in photographic waste processing. Japanese Patent Publication No. 51099854 describes the use of an oxide, hydroxide or water soluble salt of an alkaline earth metal to precipitate heavy metal ions in a photographic waste effluent.

Japanese Patent Publication No. 63291680 discloses the use of a solidifying agent in the final stage of treatment of photographic waste, wherein the solidifying agent is a hardener, such as cement, or a desiccant such as silica gel. The liquid absorbing agent is a powder or particle with a diameter of 0.01–3 mm which is not soluble in water.

The use of a water-soluble silicate, in particular an alkali metal silicate, in the field of photographic waste effluent treatment has nowhere been documented. However, it has now been found that such an addition to a photographic waste that has previously been treated by adding thereto an alkaline earth compound or another compound with an oxidation number (or valency) greater than one, such as manganese, with or without other additions, hardens it over a period of a few days and renders it glass-like. The resulting 'glass' is less permeable to water than the original solid and therefore it is less likely that polluting compounds will wash out from the treated waste compound compared to that which is untreated. Consequently the precipitated photographic waste is more convenient and safer to transport and less harmful to the environment if used for landfill. Moreover, the process is inexpensive and any waste spillage is much easier to remove.

The effluent to be treated may, for example, have arisen from any of the photographic processes described in Item 308119, Research Disclosure December, 1989, Industrial Opportunities Ltd., Hants., U.K., and especially sections XIX, XX and XXIII thereof.

The method applies to any solid waste that has been generated by adding an alkaline earth compound, or another compound with an oxidation number greater than one, to processing solutions in order to precipitate metals and/or oxysulphur compounds. For example waste generated by addition of calcium hydroxide or a mixture of calcium salts and another metal hydroxide, may be particularly suitable. However it is important for the processing solution not to contain ammonium ions to prevent liberation of free ammonia, unless appropriate safety measures are taken.

According to the present invention therefore, there is provided a method of treating photographic effluent containing metal ions with an oxidation number greater than one, comprising the addition of a water-soluble silicate to the effluent in an amount to render it glass-like and less permeable to water.

The silicate may be added to the treated effluent suspension and the mixture separated, for example by filtration or centrifugation, or alternatively it may be added to the pre-separated solid.

Although any water-soluble silicate may be used, conveniently readily available sodium silicate ('water-glass') is used, generally in the form of its solution. The silicate may be added in an amount by dry weight from 5 to 40 g per liter of effluent, preferably in the range 10 to 20 g, conveniently as a 10 to 15% solution, especially 12%.

The invention will now be described with reference to the following example which in no way limits the scope of the invention.

EXAMPLE

A. A model processor effluent was made by combining the 300 ml of the following developer amplifier with 500 ml of a bleach-fix, also described below:

| Developer/Amplifier | |
| --- | --- |
| potassium carbonate | 20 g |
| diethyldihydroxylamine | 5 g |
| ethylenediaminetetraacetic acid (EDTA) | 1 g |
| colour developer CD3 | 4 g |
| 30% hydrogen peroxide | 5 g |
| water to | 1 liter |
| pH adjusted to 10.3 with sulphuric acid or NaOH | |
| Bleach-fix: | |
| sodium iron (III) EDTA | 20 g |
| sodium thiosulphate | 50 g |
| sodium sulphite | 20 g |
| acetic acid | 20 ml |
| water to | 1 liter |
| the pH was adjusted to 5.5 with acetic acid. | |

0.8 g of silver chloride was added to this mixture and this was stirred until it had dissolved. The mixture was left to stand overnight to allow most reactions to complete.

100 ml of this model effluent was poured into a 250 ml beaker. To this was added 4 ml of hydrogen peroxide to reduce the oxygen demand of the mixture by converting the reducing sulphur compounds to their oxidised form. This mixture was stirred for two minutes to allow the reactions to complete, 2.8 g of calcium hydroxide was then added to the mixture to precipitate the iron and most of the oxidised sulphur compounds. Following this, 2 g of activated charcoal was added to remove colour developing agents and their derivatives, and also the diethylhydroxylamine. After one minute stirring, 10 g of Zerolit TM FFip ion-exchange resin was added to remove the sequestering agent, EDTA, and also to reduce the pH by partial removal of hydroxide ions.

The mixture was filtered by standard means using fast filter paper.

B. 10 g of damp solid generated as in (A) was taken and 2 g of 12% sodium silicate solution added. The mixture was stirred and then allowed to stand in a suitable plastic container for two days. The mixture turned solid and could be knocked out of the container as a glass-like pellet.

We claim:

1. A method of treating photographic effluent, comprising:

introducing one or more compounds comprising a metal ion with an oxidation number greater than one, to said photographic effluent, to form an effluent suspension of heavy metal and oxysulfur precipitates in an effluent liquor, and adding a water-soluble silicate either to said precipitates following separation of said precipitates from said effluent liquor, or to said effluent suspension, whereby said precipitates are converted to a hard, glass-like solid which is less permeable to water than said precipitates.

2. A method as claimed in claim 1, further comprising separating said glass-like solid from said effluent liquor by standard methods.

3. A method as claimed in claim 1, wherein said precipitates are separated from said effluent liquor by standard methods.

4. A method as claimed in claim 1, wherein the silicate is sodium silicate.

5. A method as claimed in claim 1, wherein the silicate is added in an amount of from 5 to 40 g, preferably 10 to 20 g per liter of effluent.

6. A method as claimed in claim 1, wherein the silicate is a silicate solution.

7. A method as claimed in claim 6, wherein the silicate solution is a 10 to 15% solution.

8. A method as claimed in claim 7, wherein the silicate solution is a 12% solution.

9. A method as claimed in claim 1, wherein at least one of the metal ions is an alkaline earth metal ion.

10. A method as claimed in claim 9, wherein the metal ion is calcium ion.

* * * * *